United States Patent
Terwilliger

(10) Patent No.: US 6,283,925 B1
(45) Date of Patent: Sep. 4, 2001

(54) BIOPSY NEEDLE HANDLE

(75) Inventor: Richard A. Terwilliger, Estes Park, CO (US)

(73) Assignee: Medical Device Technologies, Inc., Gainesville, FL (US)

( * ) Notice: Subject to any disclaimer, the term of this patent is extended or adjusted under 35 U.S.C. 154(b) by 0 days.

(21) Appl. No.: 09/076,181

(22) Filed: May 12, 1998

(51) Int. Cl.⁷ .................................................. A61B 10/00
(52) U.S. Cl. ............................................. 600/568; 600/562
(58) Field of Search .................................. 600/568, 562, 600/564, 565, 566, 567

(56) References Cited

U.S. PATENT DOCUMENTS

| Re. 34,056 | 9/1992 | Lindgren et al. . |
|---|---|---|
| 3,090,384 | 5/1963 | Baldwin et al. . |
| 3,732,858 | 5/1973 | Banko . |
| 3,788,320 | 1/1974 | Dye . |
| 3,844,272 | 10/1974 | Banko . |
| 4,210,146 | 7/1980 | Banko . |
| 4,266,555 | 5/1981 | Jamshidi . |
| 4,403,617 | 9/1983 | Tretinyak . |
| 4,469,109 * | 9/1984 | Mehl ..................................... 600/566 |
| 4,476,864 | 10/1984 | Tezel . |
| 4,570,632 | 2/1986 | Woods . |
| 4,600,014 | 7/1986 | Beraha . |
| 4,640,296 | 2/1987 | Schnepp-Pesch et al. . |
| 4,651,752 | 3/1987 | Fuerst . |
| 4,655,226 | 4/1987 | Lee . |
| 4,699,154 | 10/1987 | Lindgren . |
| 4,733,671 | 3/1988 | Mehl . |
| 4,747,414 | 5/1988 | Brossel . |
| 4,776,346 | 10/1988 | Beraha et al. . |
| 4,817,631 | 4/1989 | Schnepp-Pesch et al. . |
| 4,838,282 * | 6/1989 | Strasser et al. ........................ 600/567 |
| 4,924,878 | 5/1990 | Nottke . |
| 4,958,625 | 9/1990 | Bates et al. . |
| 5,025,797 | 6/1991 | Baran . |
| 5,064,411 | 11/1991 | Gordon, III . |
| 5,220,926 | 6/1993 | Jones . |
| 5,316,013 | 5/1994 | Striebel, II et al. . |
| 5,415,182 * | 5/1995 | Chin et al. ............................ 600/567 |

FOREIGN PATENT DOCUMENTS

| 0010321 | 4/1980 | (DE) . |
|---|---|---|
| 0141108 | 4/1980 | (DE) . |
| 709714 | 2/1954 | (GB) . |
| 748451 | 2/1956 | (GB) . |
| 175611 | 9/1965 | (RU) . |
| WO 83/03343 | 10/1983 | (WO) . |

* cited by examiner

*Primary Examiner*—Max Hindenburg
*Assistant Examiner*—Brian Szmal
(74) *Attorney, Agent, or Firm*—Fliesler, Dubb, Meyer & Lovejoy LLP

(57) ABSTRACT

A novel handle assembly has an opening that allows for the insertion of a needle set. The needle set is an integral unit and consists of an outer hollow cannula and an inner pointed tip stylet. The stylet and the cannula are capable of being urged forward separately into the biopsy area in a defined motion in relation to each other. The handle assembly includes a housing, and a slidable extension. In operation, the stylet and the cannula are inserted into the housing. The extension is moved rearward until the cannula is in a spring loaded position and a first locking member has engaged a second locking member. An adjustable wheel on the extension is turned to set the stylet to a predetermined distance for insertion into the biopsy area. The stylet and the cannula are inserted into a patient near the biopsy area. The stylet is then urged into the biopsy area to the predetermined depth. The slidable extension is pushed forward by a user's thumb and the cannula is fired so that the tissue is severed and captured in the notch of the stylet. After disengaging the biopsy area, the stylet is pressed forward using the extension so that the tissue sample is exposed and may be removed. The stylet is then pulled back into the starting position so that multiple samples may be taken.

26 Claims, 13 Drawing Sheets

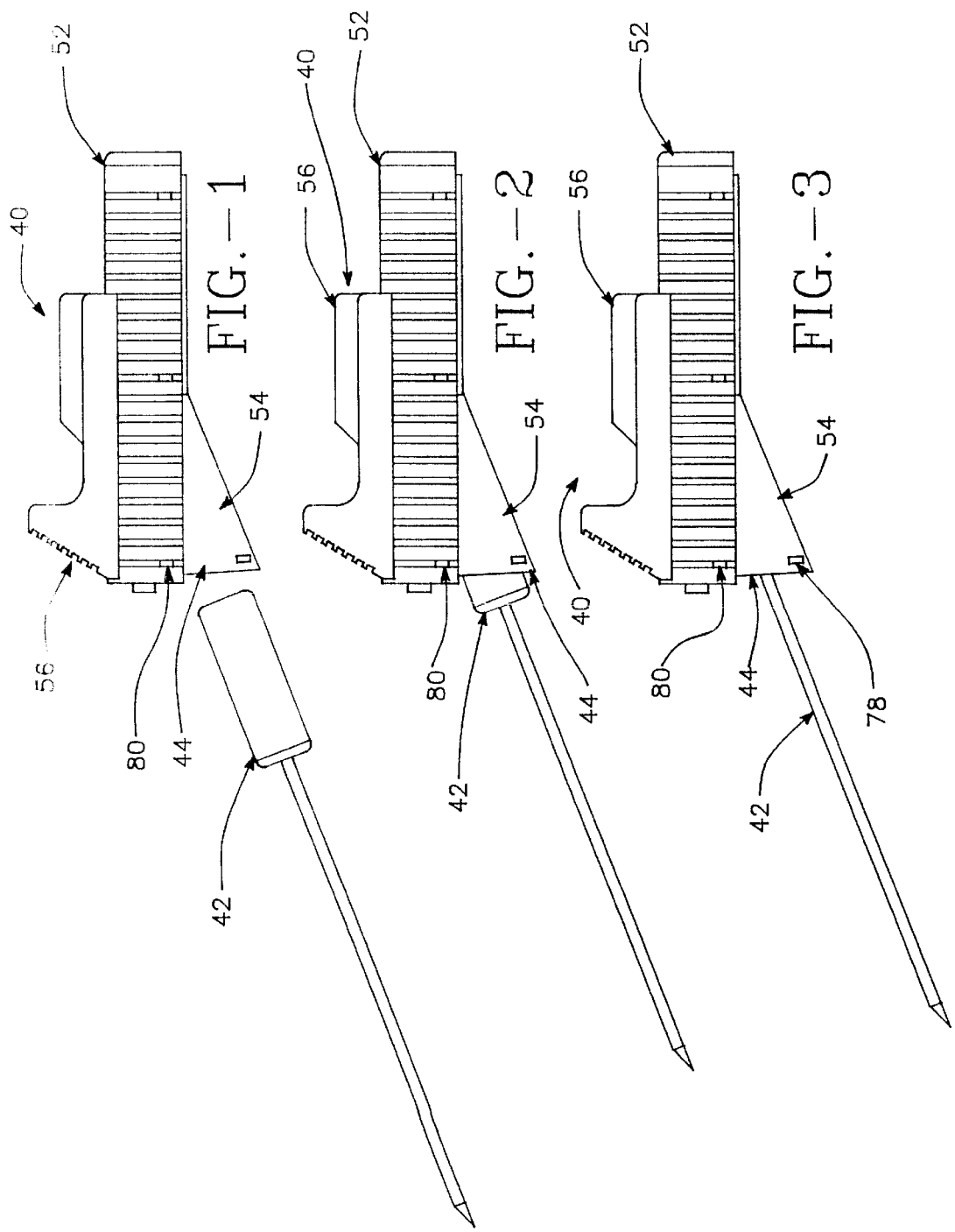

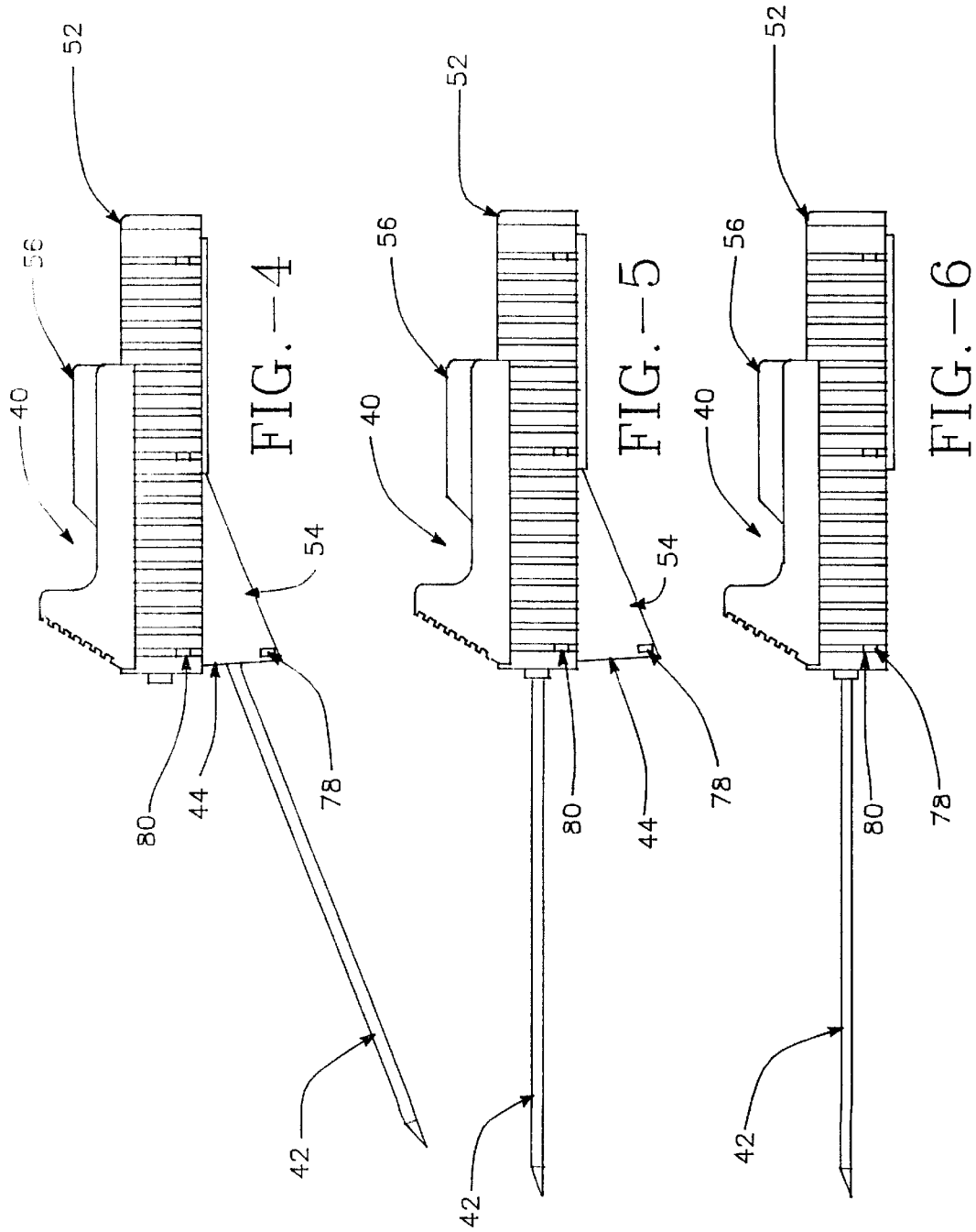

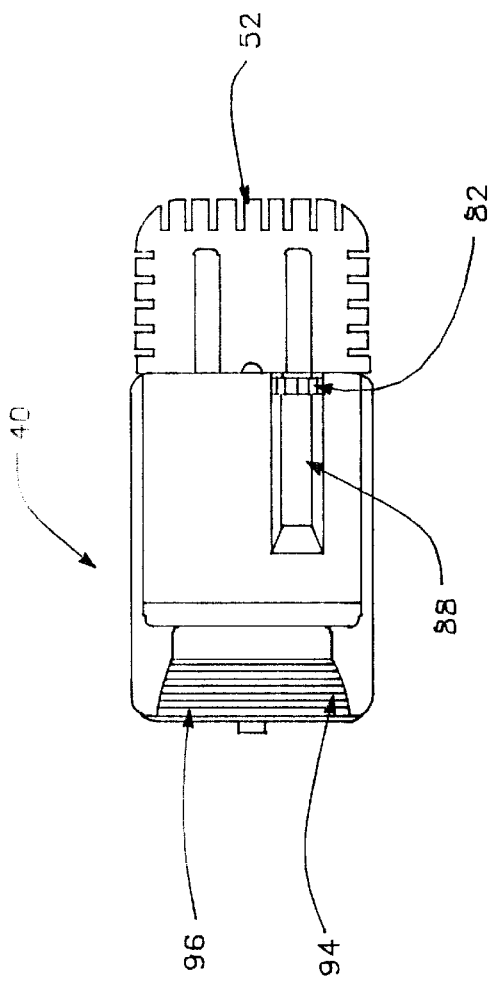
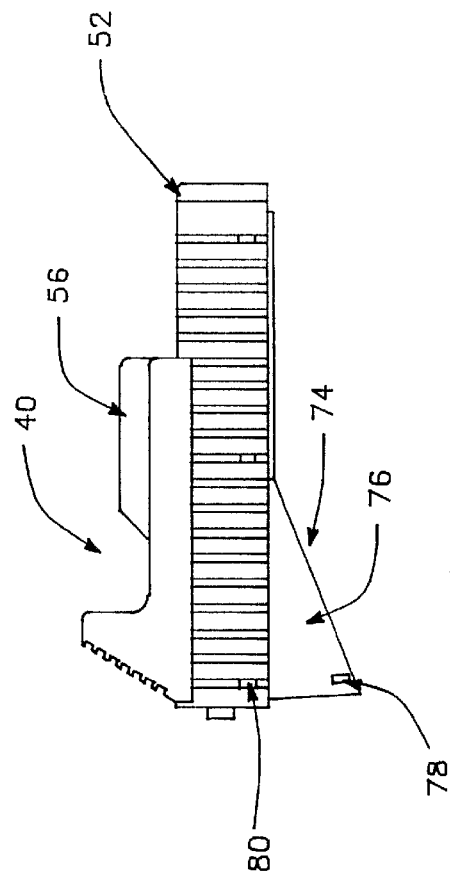
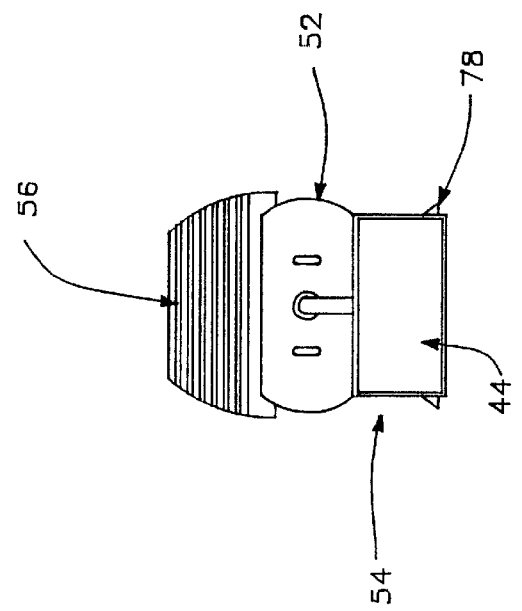

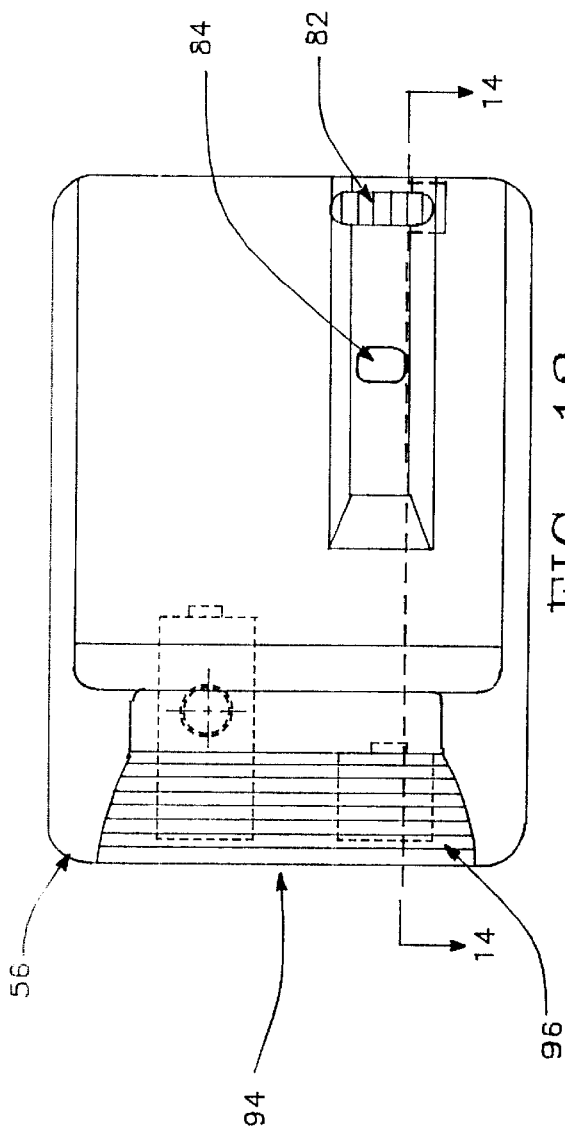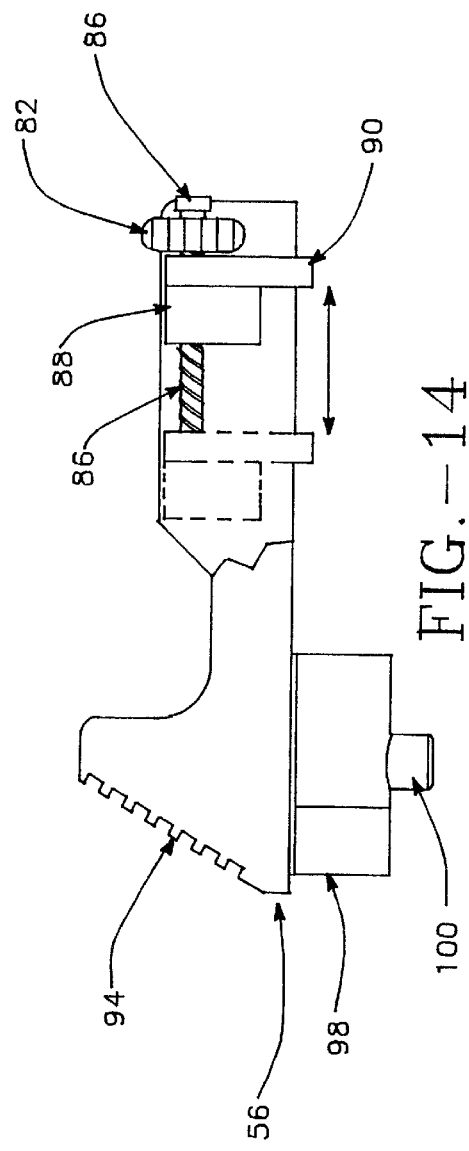
FIG.-13
FIG.-14

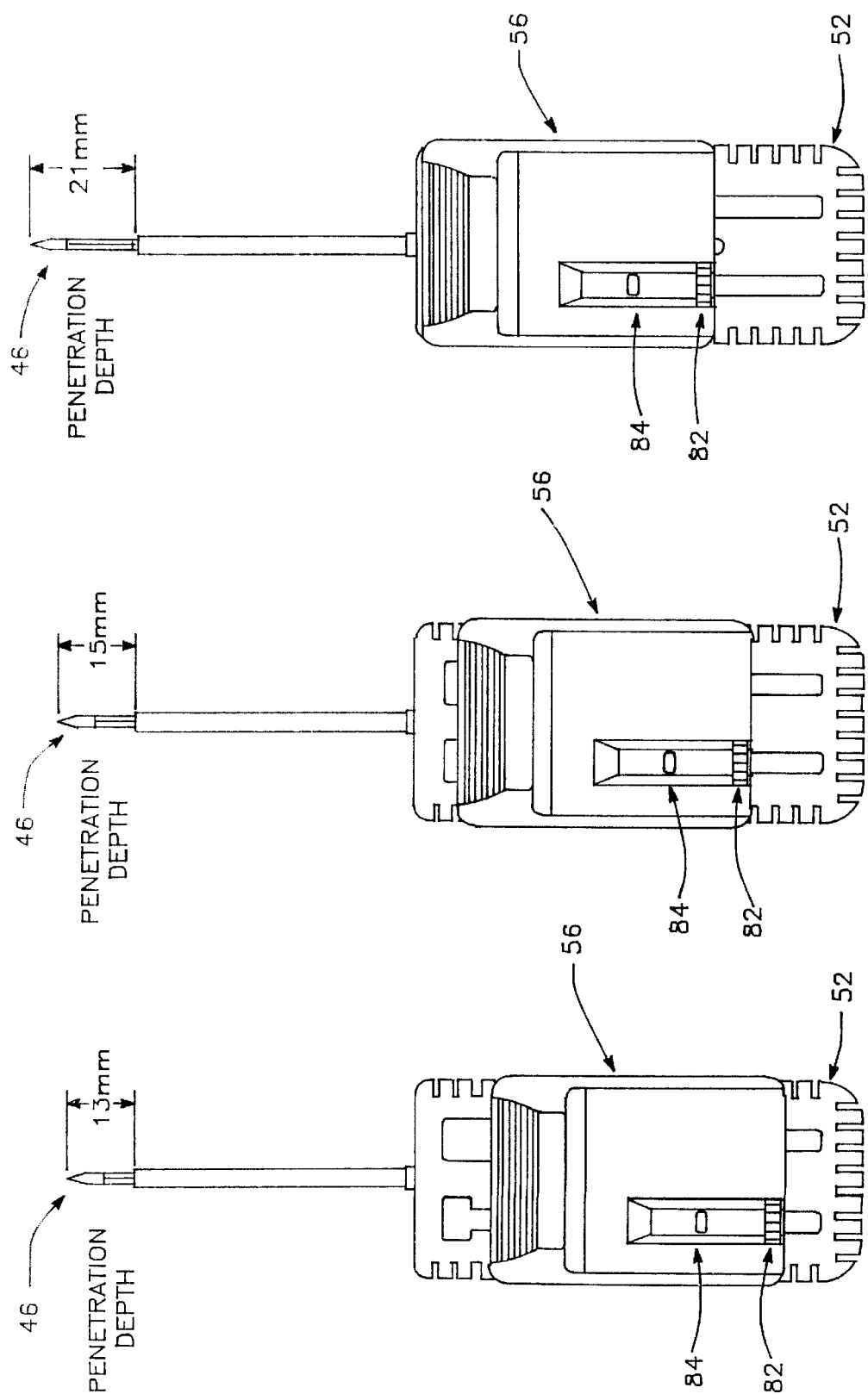

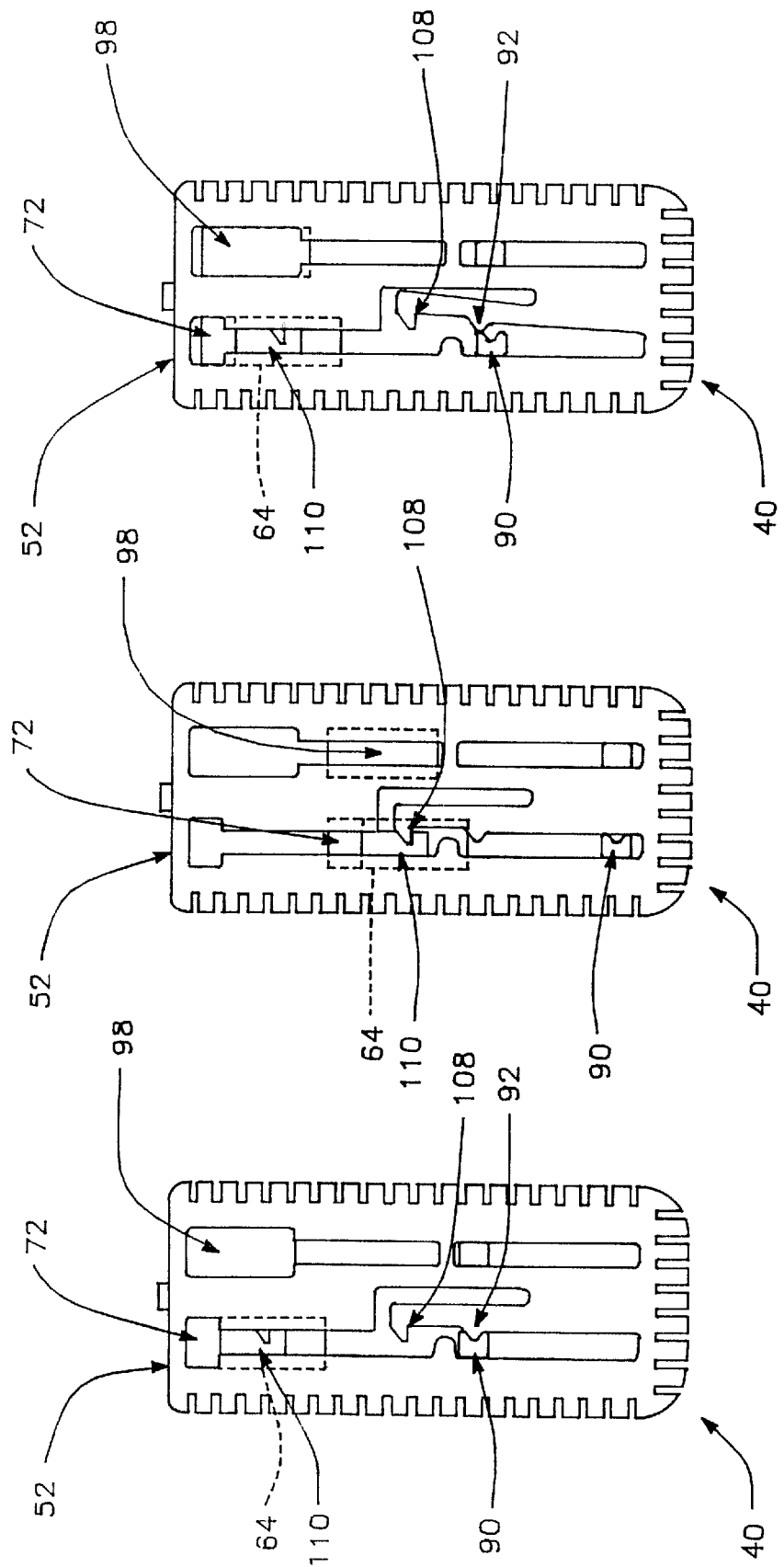

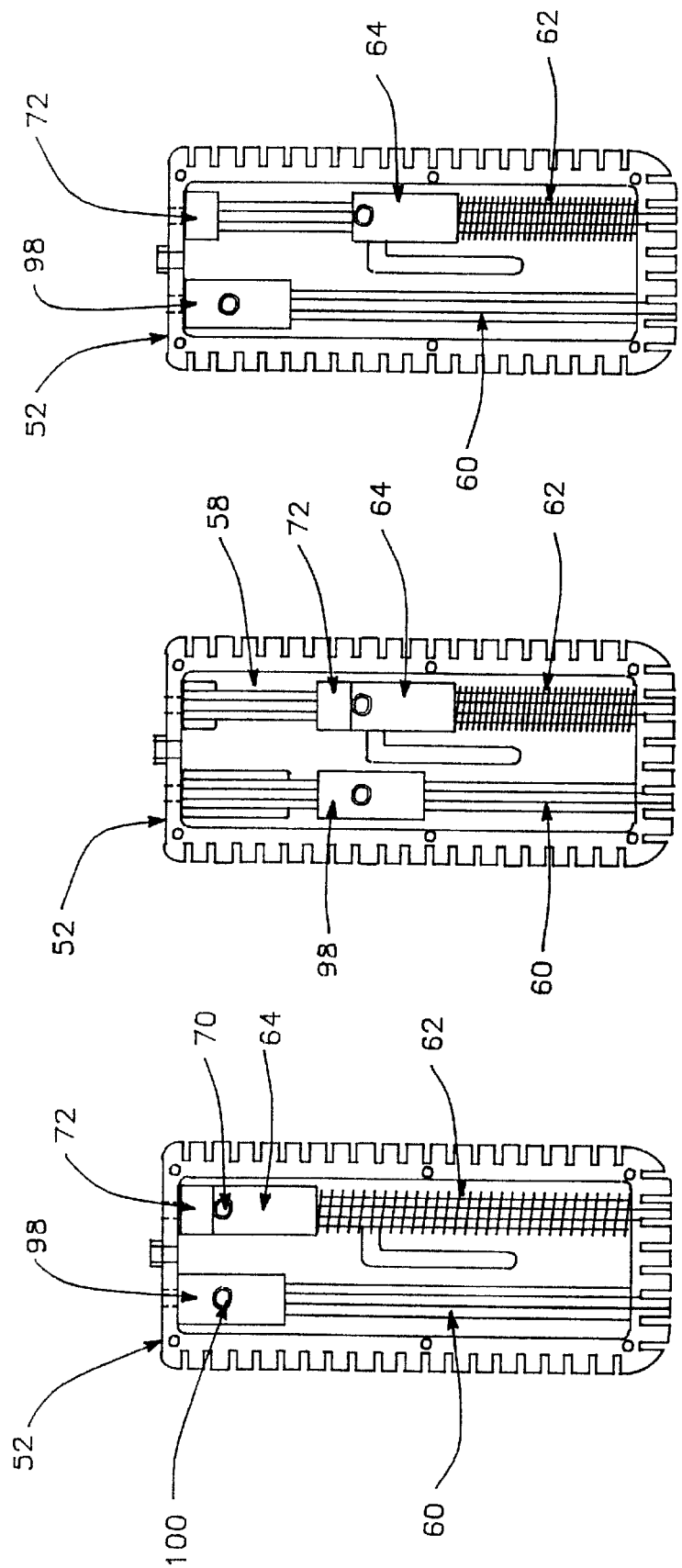

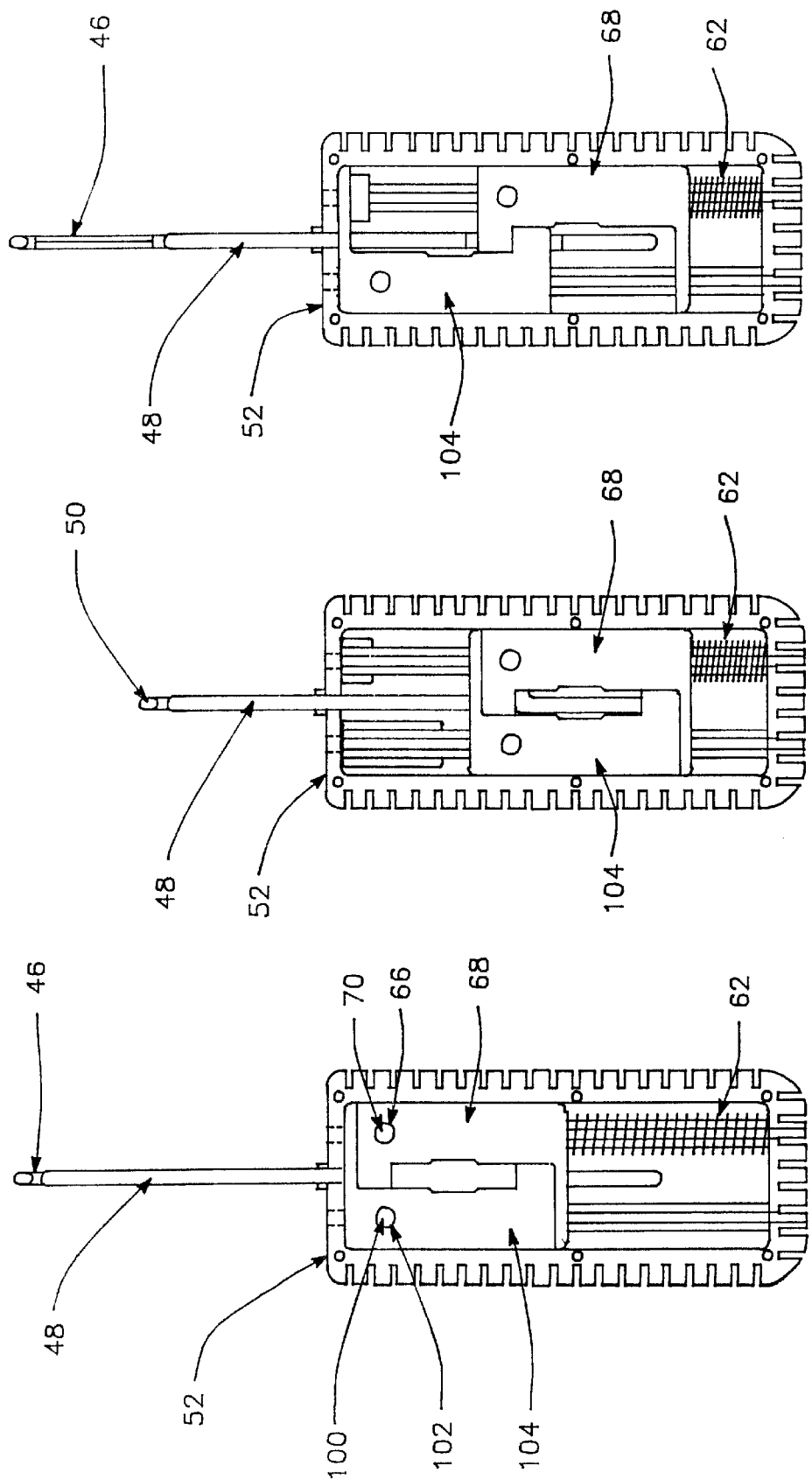

INSTALLATION OF PRIOR ART NEEDLE SET INTO INVENTIVE HANDLE

SEQUENCE OF HAND ACTIONS TO PERFORM BIOPSY AND RETRIEVE SAMPLE
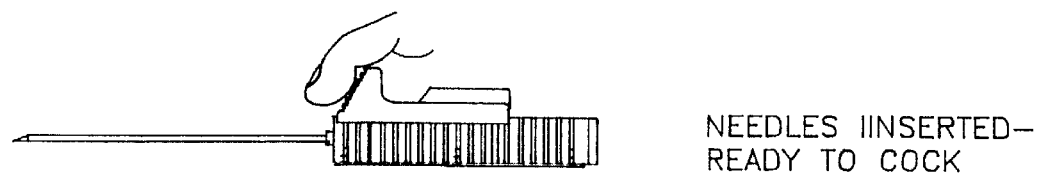
NEEDLES IINSERTED—
READY TO COCK
FIG.—28a
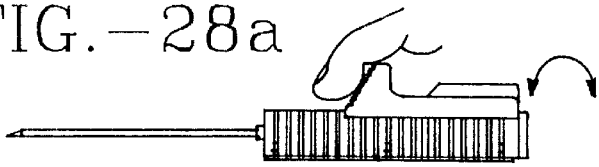
COCKED— ADJUST
WHEEL TO SET
STYLET EXTENSION
FIG.—28b
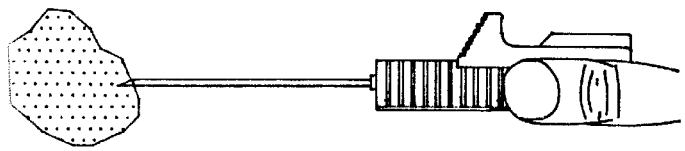
INSERT INTO
BIOPSY AREA
FIG.—28c
PRESS STYLET OUT—
INTO BIOPSY SITE
FIG.—28d
FINAL PUSH
FIRES CANNULA
FIG.—28e
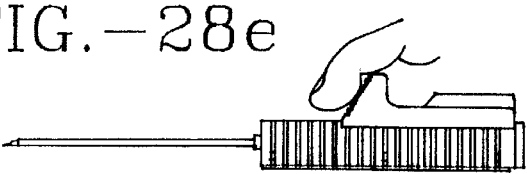
RECOCK AFTER
BIOPSY
FIG.—28f
PRESS STYLET
FORWARD TO
REMOVE SAMPLE
FIG.—28g
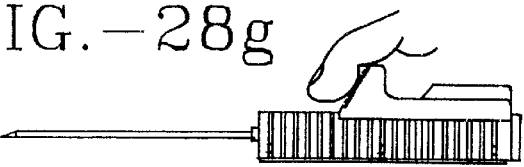
PULL BACK STYLET
READY TO BIOPSY
FIG.—28h

BIOPSY NEEDLE HANDLE

FIELD OF THE INVENTION

This invention relates to an automated mechanism to collect a tissue sample from humans or animals by a procedure referred to as tissue biopsy and more particularly to an improved handle assembly which can be used in semi-automated biopsy procedures to assist in the extraction of tissue sample of a predetermined size in a precise and rapid manner.

BACKGROUND OF THE INVENTION

It is often desirable and frequently absolutely necessary to sample or test a portion of tissue from humans and even animals to aid in the diagnosis and treatment of patients with cancerous tumors, pre-malignant conditions and other diseases or disorders. Typically in the case of cancer or the suspicion of malignant tumors, a very important process called tissue biopsy is performed to establish whether cells are cancerous.

Biopsy may be done by an open or closed technique. Open biopsy removes the entire tissue mass or a part of the tissue mass. Closed biopsy on the other hand is usually performed with a needle-like instrument and may be either an aspiration (hollow needle on a syringe) or a core biopsy (special tissue cutting needle design). In needle aspiration biopsy, individual cells or clusters of cells are obtained for cytologic examination. In core biopsy, a segment of tissue is obtained for histologic examination which may be done as a frozen section or paraffin section.

The methods and procedures of obtaining tissue samples for cytologic or histologic examination have been performed historically by manual insertion and manipulation of the needle. These procedures are performed "blind" by the physician and guided by "feel" and known anatomic "landmarks".

Tumors are first noted in a patient by one of three ways, palpation, x-ray imaging or ultrasound imaging. Once a tumor is identified, a biopsy procedure is performed. Modern medical opinion dictates early detection of cancer, which increases the likelihood of successful treatment. Biopsy are performed on "Tumor Masses" as small as 2 millimeters in diameter. This procedure is performed under ultrasound or x-ray guidance. Tumors of this size cannot be biopsied reliably by hand since the tumor is about the same size as the biopsy needle. Manual attempts at biopsy can push the tumor away without piercing the mass. Automatic puncture devices are needed to accelerate the needle at such a velocity that even a small tumor can be pierced.

Two very important innovations in the field of medical technology have influenced the field of tissue biopsy in the last five years.

One, the use of tissue imaging devices which allow the physician to "see" inside the body and visually guide the needle to the tumor mass.

Two, the invention of the Automatic Core Biopsy Device (ACBD) or "Biopsy Gun". The ACBD is an instrument which propels a needle set with considerable force and speed to pierce the tumor mass and collect the tissue sample. This ACBD device has allowed physicians to test tissue masses in the early stages of growth and has contributed to the medical trend of early diagnosis and successful treatment of cancer.

Examples of such ACBD devices have been described with respect to the collection of tissue samples in U.S. Pat. Nos. 4,651,752, 4,702,260, and 4,243,048.

Historically, Automated Core Biopsy Devices (ACBD) have used the "Tru-Cut" needle set design. The "Tru-Cut" needle is comprised of an inner notched stylet with an outer cannula. The stylet is advanced into the tissue under spring power followed by the cannula which cuts and traps the tissue sample in the notch of the stylet. The "Tru-Cut" needle yields a core sample which is semi-circular in cross section, with length of the core sample determined by the stroke of the ACBD.

The stylet is a needle with a notched cut out at the distal end. The cannula is a hollow needle with an angled cutting surface at the distal end which slides over the stylet. When the stylet is pushed into tissue, the tissue is pierced and relaxes into the notched cut out. When the cannula is slid forward, the tissue in the notch of the stylet is sliced off and retained in the notch until the cannula is drawn back.

Subsequent improvements to the "Tru-Cut" needle design have been introduced and are described in U.S. Pat. No. 5,449,001.

In certain biopsy procedures where the suspect mass is in close proximity to main arteries or where potential damage could occur from the rapid automated advance of the stylet on the ACBD, it is often desirable for the physician to manually place the inner stylet of the needle set into the biopsy area and cut the prolapsed tissue with the advancement of the cannula. This process is commonly referred to as closed "semi-automated" biopsy, due to the fact that the stylet is manually deployed and the cannula is automatically advanced under spring power.

There are numerous prior art devices on the market that employ this semi-automated process. However, in prior art designs, if the physician requires a biopsy device which cycles the needle set a short or longer distance into the tissue mass, a separate device for each needle distance desired has to be purchased. Current prior art devices have captive needle sets which require the physician to have many different styles of devices available to perform the range of procedures that are encountered in a biopsy procedure. These prior art devices are typically a small disposable plastic frame that houses a spring to power the cannula and a push rod to manually deploy the stylet. The stylet and cannula are integral to the plastic frame and cannot be removed. These prior art devices are supplied with a specific needle gauge, needle length and predetermined extension of the stylet for each individual device. This is a design limitation because it creates a situation of compromise between the physician's desire to use the optimum needle for a given procedure and the need to overstock all the possible combinations of needle gauges, lengths and predetermined extensions of the stylet that are available for a biopsy procedure. Furthermore, in the era of managed health care, the cost of biopsy procedures has come under scrutiny. The disposable single use devices are expensive and not desirable due to their high single use cost.

Accordingly, each biopsy procedure, given the anatomic location of the biopsy area and tissue density, requires a particular needle gauge, a specific needle length and a predetermined extension of the stylet into the tissue to obtain the optimum biopsy sample for that particular procedure. Thus, prior art designs of the ACBD have a need for a design that allows the interchangeability of the needle sets to accommodate the parameters of the biopsy procedure to be performed.

On the other hand, the physician may use a prior art device that is capable of functioning at different distance settings to perform a range of biopsy procedures. However, such an adjustable device is mechanically complicated and requires external settings to be made to allow the mechanism to perform at different needle advancement distances. Also the reusable handles have, in prior art, been costly to obtain because of the expense of manufacturing a complicated mechanical design. Since the mechanism of the prior art ACBD is designed to have a stylet that moves forward first and then activates the cannula, thus advancing the needles in their proper sequence, these prior art devices require many high tolerance mechanical moving parts with precision bushings in order to have the device operate properly. The required repeated use of the reusable design dictates that the mechanical design be robust and operates many cycles without undue wear or failure. These requirements have produced in prior art, ACBDs that are heavy, large and costly due to their complicated mechanical designs.

Thus, the size, weight and expense of single use and reusable prior art ACBD's have limited their use. An improved design is needed that gives the physician a small, light weight, easy to operate and cost effective design that improves the function of obtaining a tissue sample of a predetermined size.

SUMMARY OF THE INVENTION

It is therefore an advantage of the present invention to provide a handle assembly for a needle set which allows a tissue sample of a predetermined size to be obtained from a tissue mass, and also which automatically captures and allows the removal of a tissue sample for examination in one operation.

It is another advantage of the present invention to provide a handle assembly which can reliably obtain biopsy samples, is simple in design, easy to use, and cost effective.

It is a further advantage of the present invention to provide a handle assembly for a needle set with a mechanism to single-handedly extend the stylet manually into the biopsy area and thus allow for single-handed operation.

It is another advantage of the present invention to provide a handle assembly for a needle set which allows the user to choose the parameters of the needle set to be used to obtain the optimal tissue samples for any given biopsy procedure.

It is a further advantage of the present invention to provide a handle assembly for a needle set with a spring powered member to actuate the cannula to assist in severing the tissue from the surrounding biopsy area.

It is yet another advantage of the present invention to provide a handle assembly for a needle set which is single patient use and disposable, and can be delivered sterilized prior to the biopsy procedure.

It is still a further advantage of the present invention to provide a handle assembly for a needle set which can be used to obtain multiple tissue samples from the same biopsy area.

In accordance with the present invention and new and improved handle for a needle set is provided. The handle assembly has an opening that allows for the insertion of a needle set. The needle set consists of an outer hollow cannula and an inner pointed tip stylet.

The handle assembly includes a housing, a locking lid, and a slidable extension. The housing is rectangular in shape and has attached to it the extension on the top and the locking lid on the bottom, which both shield the inner mechanism. Inside the housing are two cylindrical rods which guide the stylet and cannula when a biopsy is performed and a tissue sample retrieved. The rod which guides the cannula has mounted thereon a spring and a cannula coupling for securing the cannula in the housing. The cannula includes an aperture in its base for connecting to a protrusion on the cannula coupling. The cannula coupling is pushed against the spring by a cannula pushing member, which is attached to the extension, until it reaches a position wherein the cannula is spring loaded and ready for release. Once the cannula is released, the spring urges the cannula forward in a rapid motion severing the prolapsed tissue which resides in the notch of the stylet.

The locking lid covers the bottom of the housing and has a descending portion having side walls which provides the opening for insertion of the needle set. The side walls include a catch on each side which engage a cut-out located on each side of the housing. Once the needle set is inserted, the descending portion is pushed up to be flush with the bottom of the housing and the needle set is secured inside the housing by engagement of the catch and cut-out on each side of the housing. The locking lid ensures one patient use of the biopsy needle.

The slidable extension covers the top of the housing and includes an adjustable wheel on the rear end which allows a tissue sample of a predetermined size to be obtained during a biopsy procedure. The extension advantageously adapts the handle to one-hand operation by the user. The slidable extension is pushed rearward on the housing until the cannula is locked in place in the spring loaded position. The adjustable wheel on the rear end of the slidable extension is then turned to the desired penetration depth. The adjustable wheel allows the user to choose the parameters of the needle set to be used to obtain an optimal tissue sample for any given biopsy procedure. The adjustable wheel is attached to the slidable extension by a screw member. Located on the screw member is a trip bar. The trip bar includes a protrusion and moves forward along with the slidable extension until the desired preset penetration depth is obtained. The slidable extension, together with the trip bar are pushed forward, thus urging the needle forward the preset length, until the trip bar protrusion interacts with a locking member protrusion to release the cannula.

At the front of the slidable extension, a pushing portion is provided. The pushing portion includes ribs for enhanced friction between the user's thumb and the pushing portion during the biopsy procedure. Located on the bottom of the slidable extension near the front is a needle coupling for engaging the stylet in the housing. The needle coupling includes a protrusion which is inserted into an aperture located on the base of the stylet.

In operation, the stylet and cannula are inserted into the handle assembly in the descending portion of the locking lid, which is then pushed upward and secured via the catch and the cut-out located on each side of the locking lid and the housing, respectively. The slidable extension is moved rearward, with a single user's hand, until the cannula is in the spring loaded position and the first locking member has engaged the second locking member. The adjustable wheel on the extension is turned to set the stylet to a predetermined distance for insertion into the biopsy area. With the same single user's hand, the stylet and the cannula are inserted into the patient near the biopsy area. The stylet is then urged into the biopsy area the predetermined distance by pushing the slidable extension forward with the user's thumb. The cannula is released and fired when the predetermined distance is reached and the tissue is severed and captured in the notch of the stylet. The stylet and the cannula are both moved rearward by the extension, thereby disengaging the biopsy area. The stylet is pressed forward using the extension so that the tissue sample is exposed and may be removed. The stylet is then pulled back into the starting position. Moving the extension rearward again reestablishes the stylet and the cannula in relation to each other in order to allow subsequent reinsertions into the biopsy area for additional tissue samples. Accordingly, the inventive biopsy handle allows the user the ability to take multiple tissue samples conveniently and quickly using only a single hand.

BRIEF DESCRIPTION OF THE DRAWINGS

The above and other advantages of the present invention will be apparent upon consideration of the following detailed description, taken in conjunction with the accompanying drawings, in which like reference characters refer to like parts throughout, and in which:

FIGS. 1–6 are side views of an embodiment of the handle assembly of the present invention showing insertion and securing of the needle set into the locking lid and housing according to the present invention;

FIG. 9 is a top view of an embodiment of a slidable extension attached to a housing according to the present invention;

FIG. 10 is a side view of an embodiment of the handle assembly showing the housing, the slidable extension and a locking lid according to the present invention;

FIG. 11 is a front view of an embodiment of the handle assembly showing the locking lid extended in an open position according to the present invention;

FIG. 13 is a top view of an embodiment of the slidable extension of the handle assembly illustrating the numeric indicator and window according to the present invention;

FIG. 14 is a broken away view of an embodiment of the slidable extension of the handle assembly through lines 14—14 of FIG. 13 according to the present invention;

FIG. 15 is a top view of an embodiment of a housing assembly having a needle set showing a needle extended 13 mm according to the present invention;

FIG. 16 is a top view of an embodiment of the housing assembly having the needle set showing the needle extended 15 mm according to the present invention;

FIG. 17 is a top view of an embodiment of the housing assembly having the needle set showing the needle extended 21 mm according to the present invention;

FIGS. 18–20 are top views showing an embodiment of the inner mechanisms of the slidable extension and the housing at various stages of taking a biopsy sample according to the present invention;

FIGS. 21–23 are inside bottom views of an embodiment of the housing at various stages of taking a biopsy sample according to the present invention;

FIGS. 24–26 are inside bottom views of an embodiment of the housing having a needle set at various stages of taking a biopsy sample according to the present invention; and FIGS. 27a to 27e, and 28a to 28h are side views of an embodiment of the handle assembly having a needle set illustrating insertion of the needle set and the sequence of stages in retrieving a tissue sample according to the present invention.

DETAILED DESCRIPTION OF THE PREFERRED EMBODIMENT

The present invention will now be described with reference to FIGS. 1 through 28 which in general relate to a novel handle assembly which can be used in a semi-automated biopsy procedure to assist in the extraction of tissue in a precise manner using only one of a user's hands. It is understood that the principles of the present invention may be suitable for a variety of functions and incorporated into various biopsy devices.

Figure 8:
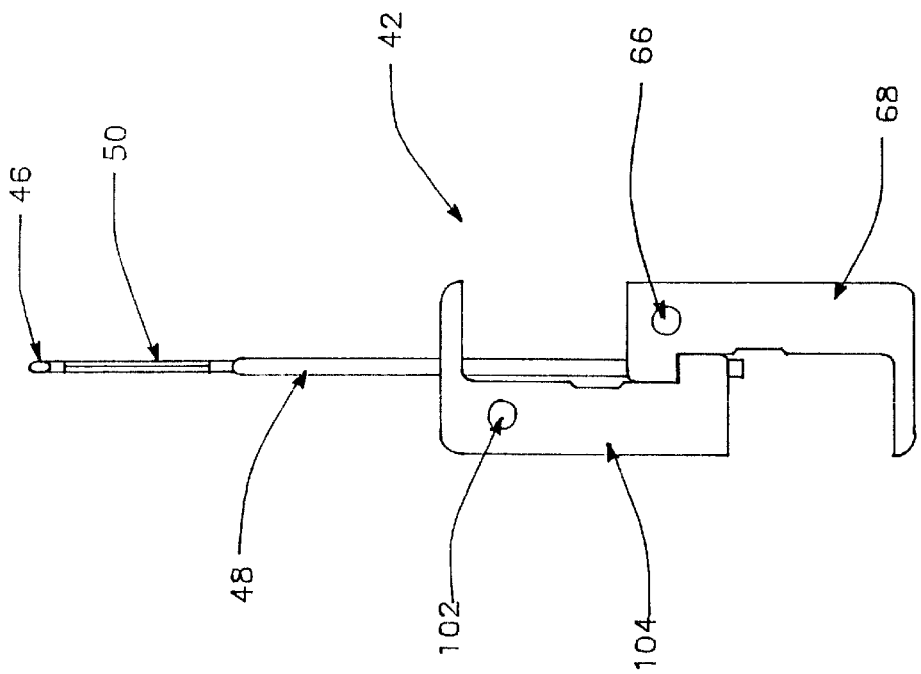
FIGS. 7–8 are top views of a needle set.
Figure 7:
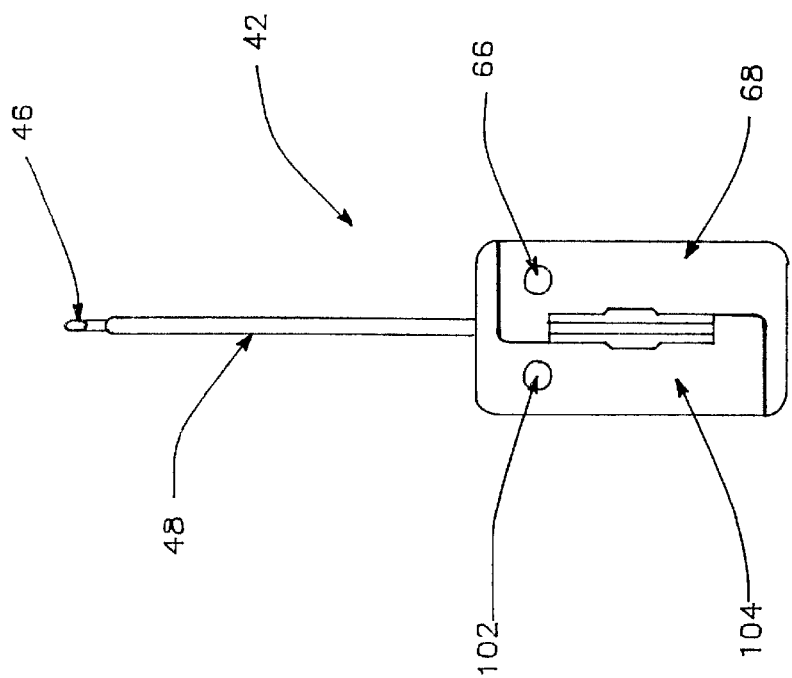

Referring now to FIGS. 1 through 8, there is shown a handle assembly 40 and a needle set 42. The handle assembly 40 has an opening 44 that allows for the insertion of the needle set 42 as will be explained hereinafter. The needle set 42 (which is not part of this invention) is an integral unit and consists of an inner pointed tip stylet 46 and an outer hollow cannula 48, as shown in FIGS. 7 and 8. The stylet 46 and the cannula 48 are capable of being urged forward separately into the biopsy area in a defined motion in relation to each other. The stylet 46 includes a notch 50 which is ground at the distal end of the needle and is a repository for the tissue that is pierced by a forward motion of the needle. The secondary motion of the cannula 48 coaxially over the stylet 46 cuts and captures the tissue in the notch 50 of the needle, thus allowing the tissue to be removed from the biopsy area and examined outside the patient.

With reference to FIGS. 9 through 12, the handle assembly 40 will now be described. The handle assembly 40 includes a housing 52, a locking lid 54, and a slidable extension 56. The housing 52 is rectangular in shape and has a hollow inside. Attached to the top of the housing 52 is the single hand operated extension 56 and attached to the bottom of the housing 52 is the locking lid 54. Both shield the inner mechanisms of the handle assembly, as will be explained hereinafter. The preferred material for the handle assembly 40 is a lightweight plastic although it is understood that the handle assembly may be formed with metals, polymers and other materials. Moreover, the handle assembly may be disposable and delivered sterilized prior to the biopsy procedure.

Inside the housing 52 are two cylindrical rods 58, 60 (FIG. 22) which guide the stylet 46 and cannula 48 when a biopsy is performed and a tissue sample retrieved. The rod 58, which guides the cannula 48, includes a spring 62 and a cannula coupling 64 for engaging the cannula in the housing. The cannula 48 (FIG. 7) includes an aperture 66 in its base 68 for connecting to a protrusion or pin 70 (FIG. 21) on the cannula coupling 64. The cannula coupling 64 is pushed against the spring 62 by a cannula pushing member 72, which is attached to the extension 56 (FIG. 1), until it reaches a position wherein the cannula 48 is spring loaded (i.e. in a spring compressed state) and ready for release. The spring loaded position is obtained when a second locking member 110 (FIGS. 18–20) on the cannula coupling 64 engages a first locking member 108 as explained hereinafter. Once the cannula 48 is released, the spring 62 urges the cannula 48 forward in a rapid motion severing the prolapsed tissue which resides in the needle notch.

Figure 11A:
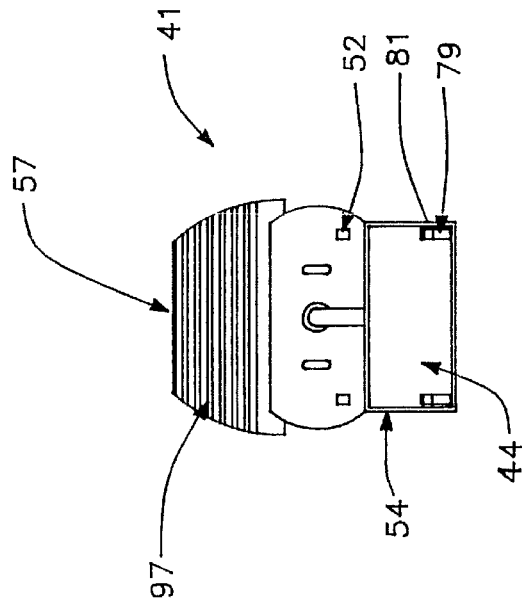
Figure 12:
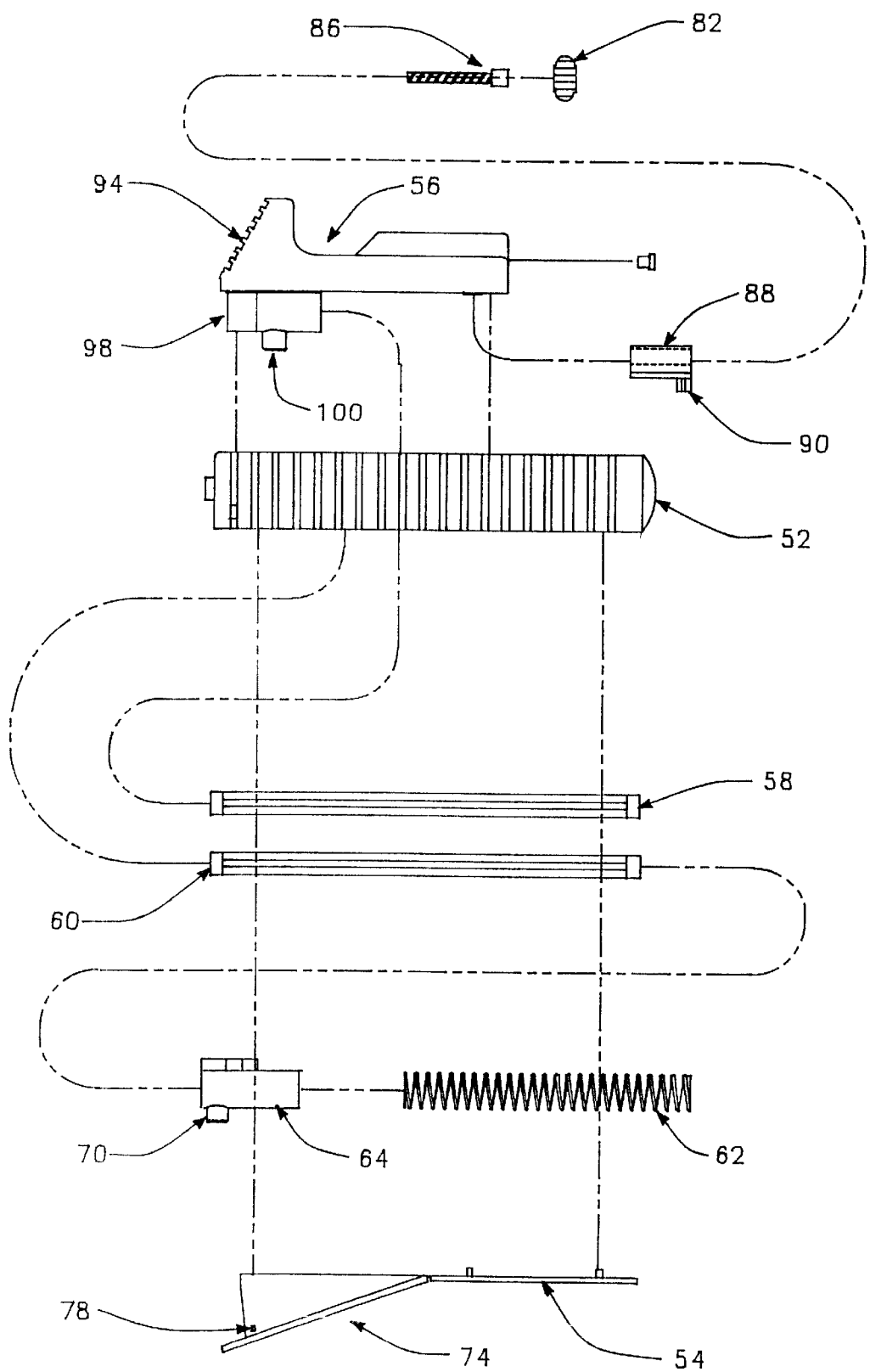
FIG. 12 is an exploded side view of an embodiment of the handle assembly according to the present invention.
Figure 27A:
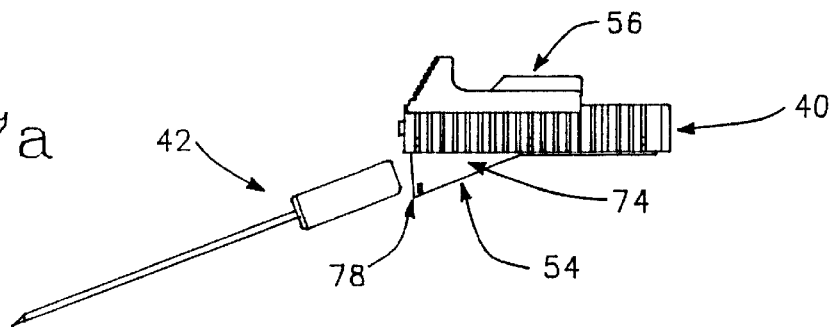
Figure 27B:
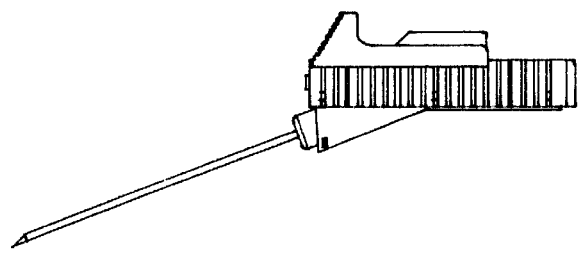
Figure 27C:
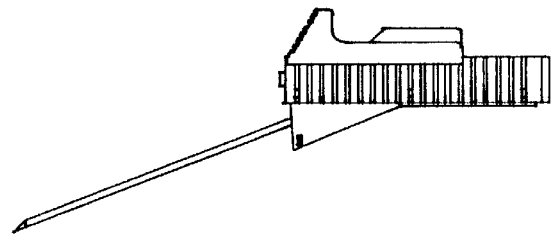
Figure 27D:
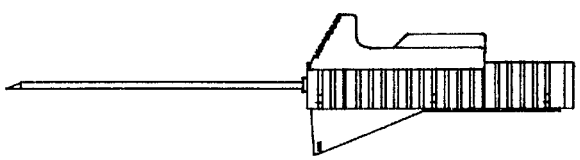
Figure 27E:
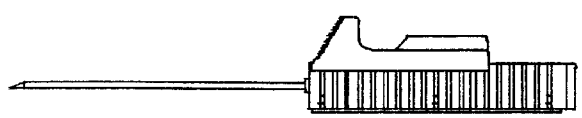

Referring now to FIGS. 10 through 12, the locking lid 54 is shown. The locking lid 54 covers the bottom of the housing 52 and has a descending portion 74 having side walls 76 which provides the opening 44 for insertion of the needle set. The side walls 76 include a catch 78 on each side which engage a cut-out 80 (FIG. 1) located on each side of the housing 52. Once the needle set is inserted, the descending portion 74 is pushed up so that it is flush with the bottom of the housing 52 and the needle set is secured inside the housing by engagement of the catch 78 and cut-out 80 on each side of the housing. The catches 78 are wedge-shaped so as to allow the catches 78 to be easily urged into the cut-outs 80. Once in place, the back edge of the wedge-shaped catches 78 snaps into and locking hold the catches in the cut-outs.

Referring now to FIGS. 13 through 17, the slidable extension 56 is shown. The slidable extension 56 covers the top of the housing 52 and includes an adjustable wheel 82 on the rear end which allows a tissue sample of a predetermined size to be obtained during a biopsy procedure. The slidable extension 56 is pushed rearward on the housing until the cannula 48 is locked in place in the spring loaded position. The adjustable wheel 82 on the rear end of the slidable extension 56 is then turned to the desired penetration depth and a corresponding numeric indicator is shown through a window 84 provided on the top of the slidable extension 56. The penetration depth may be set from 13 mm to 21 mm and is the distance that the needle 46 is urged forward into the biopsy area, as shown in FIGS. 15–17. It is to be understood that smaller and larger lengths can be possible with the same basic design as is understood by one skilled in the art. The adjustable wheel 82 is attached to the slidable extension 56 by a screw member 86. Located on the screw member 86 is a trip bar 88. When the adjustable wheel 82 is turned, the desired preset penetration depth of needle 46 is obtained. The trip bar 88 includes a protrusion or tip 90 and moves forward along with the slidable extension 56. The wheel 82 sets the position of the protrusion or tip 90 relative to the slidable extension 56. The slidable extension 56, together with the trip bar 88 are pushed forward, thus urging the stylet 46 forward the preset length, until the trip bar protrusion or tip 90 interacts with a first locking member protrusion 92 (FIG. 18) as explained hereinafter.

At the front of the slidable extension 56, a pushing portion 94 (FIG. 9) is provided. The pushing portion 94 includes ribs 96 (FIG. 13) for enhanced friction between the user's thumb and the pushing portion during the biopsy procedure. The pushing portion 94 also provides an apparatus to single-handedly extend the stylet 46 manually into the biopsy area. Located on the bottom of the slidable extension 56 near the front is a stylet needle coupling 98 for securing the stylet and the cannula pushing member 72 (FIGS. 21–23) for pushing the cannula coupling 64 against the spring 62. When the handle assembly is assembled, the stylet coupling 98 and the cannula pushing member 72 are located within the housing 52. The stylet coupling 98 includes a protrusion or pin 100 which is inserted into an aperture 102 (FIGS. 7, 8) located on a base 104 of the stylet 46.

Considering FIGS. 18 through 20, in detail, these figures depict top cross-section views of the handle assembly 40 showing the operation of the slidable extension 56 and the related internal parts. FIG. 18 shows the mechanisms of the slidable extension which moves the stylet and the cannula. The cannula pushing member 72 and the stylet coupling 98, which are attached to the slidable extension 56, are shown in a starting position. The trip bar protrusion or tip 90, the locking member protrusion 92 and the first locking member 108 are also depicted. FIGS. 19, 22, 25, shows the stylet and the cannula being forced rearward by the slidable extension 56 and the cannula pushing member 72 on the extension 56 until the first locking member 108 engages the second locking member 110 on the cannula pushing member 72 and the cannula is cocked. Once the notch of the second locking member 110 has engaged the protrusion of the first locking member 108 so that the cannula is locked in a spring loaded position (FIG. 19), and the length of the tissue sample is adjusted if desired, the slidable extension 56, and thus the stylet, is urged forward into the biopsy area by manually pushing the pushing portion 94 forward. FIG. 20 shows the trip bar protrusion 90 being moved forward by the extension 56 until the locking member protrusion 92 is deflected to the point of releasing the first locking member 108 from the second locking member 110 of the cannula coupling 64. The cannula of the needle set is then urged rapidly forward by the spring in order to sever and capture the tissue sample.

Considering FIGS. 21–23, in detail, these figures depict cross-section inside bottom views of the embodiment of the handle assembly 40. FIG. 21 shows the stylet coupling 98 and the cannula coupling 64 in the starting position. The protrusions or pins 100, 70 of stylet coupling 98 and the cannula coupling 64 are inserted into the apertures 102, 66 located on the bases of the stylet 46 and of the cannula 48, and thereby position the stylet 46 and cannula 48 relative to the housing 52 of the handle 40. The slidable extension 56 is connected to the stylet coupling 98 and the cannula pushing member 72. The rods 58, 60 are provided for guiding the stylet and the cannula in the housing 52 via the stylet coupling 98 and the cannula coupling 64, respectively. The spring 62 is also provided for powering the cannula when it severs the tissue captured in the notch of the stylet. FIG. 22 shows the stylet coupling 98 and the cannula coupling 64 being moved rearward at the point where the first locking member 108 engages the second locking member 110 (FIG. 19). The needle coupling 98, the cannula coupling 64 and the spring are guided along the rods. FIG. 23 depicts the stage where the stylet has been inserted into the biopsy area the predetermined distance (as set by wheel 82 and when the pushing portion 94 of the slidable extension 56 has been manually pushed forward) and the cannula coupling 98 and the cannula are in the spring loaded position ready to be actuated.

Considering FIGS. 24–26, in detail, these figures depict bottom cross-section views of the handle assembly 40 including the needle set 42 showing the operation of the slidable extension 56 and the related internal parts that detail the stages of the biopsy procedure. FIG. 24 shows the needle set 42 and the handle assembly 40 in the starting position. The apertures 66, 102 on both the needle and the cannula are engaged with the protrusions or pins 70, 100 on the stylet coupling and cannula coupling, respectively. FIG. 25 shows the needle 46 and the cannula 48 after the stylet and the cannula have been moved rearward and the first locking member 108 has engaged the second locking member 110 (FIG. 19). FIG. 26 shows the assembly wherein the stylet 46 has been urged forward to a predetermined distance and the cannula 48 remains in the spring loaded position ready for release.

As shown in FIGS. 27a–e, the needle set 42 is inserted into the handle assembly 40 in the descending portion 74 of the locking lid 54 which is then pushed upward and secured via the catch 78 and the cut-outs 80 located on each side of the locking lid and the housing, respectively. In single-handed operation (FIGS. 28a–h), the slidable extension 56 is moved rearward until the cannula 48 is in the spring loaded position and the first locking member has engaged the second locking member (FIG. 28b). The adjustable wheel 82 on the extension is turned to set the needle to a predetermined distance for insertion into the biopsy area (FIG. 28c). The stylet 46 and the cannula 48 are inserted into the patient near the biopsy area. The stylet 46 is then urged into the biopsy area the predetermined distance by the slidable extension 56 so that the tissue is pierced and relaxes into the notch 50 of the needle (FIG. 28d). The slidable extension is pushed forward by the user's thumb. The cannula is then actuated when the trip bar protrusion deflects the locking member protrusion. The cannula rapidly slides forward so that the tissue in the notch is severed and retained in the notch of the stylet (FIG. 28e). The stylet 46 and the cannula 48 are both moved rearward by the extension 56, thereby disengaging the biopsy area (FIG. 28f) and the needle set is removed from the patient. The stylet 46 is then pressed forward using the slidable extension 56 so that the tissue sample is exposed and may be removed. Moving the slidable extension 56 rearward again reestablishes the stylet 46 and the cannula 48 in relation to each other in order to allow subsequent reinsertions into the biopsy area for additional tissue samples.

Figure 9A:
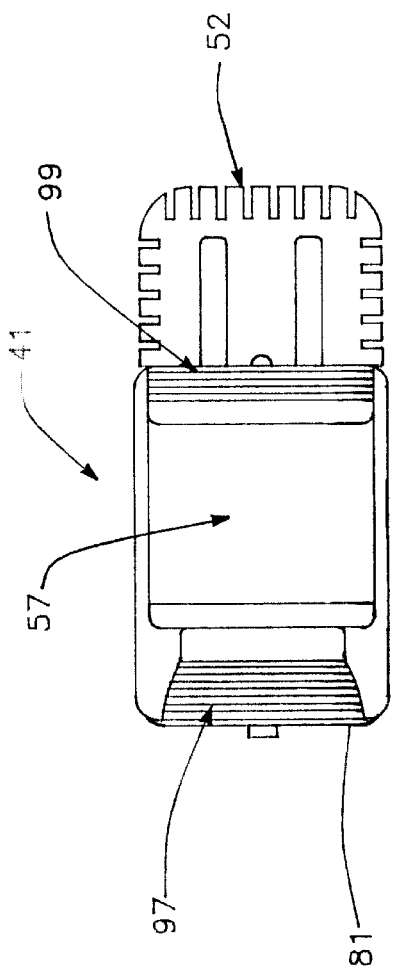
FIGS. 9a, 10a, and 11a are similar to FIGS. 9, 10, and 11 respectively, except these figures depict another embodiment of the invention which has preset the stylet to a single non-adjustable length stroke, and has a modified slide actuator and lid latch mechanism.
Figure 10A:
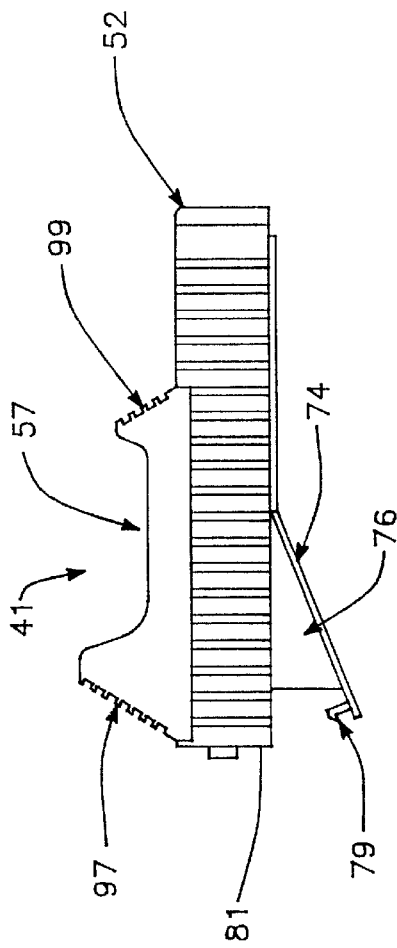

FIGS. 9a, 10a, and 11a depict another embodiment of the handle 41 where elements that are similar to the first embodiment of handle 40 are similarly numbered. Handle 41 includes an extension or actuator 57 which is slidable and operable with a single hand. Actuator has no adjusting wheel and thus handle 41 is present for a single stylet throw length and thus a single tissue sample length. Actuator 57 includes first and second upstanding protrusions 97, 99 which can be engaged by, for example, a thumb to push the actuator back and forth with respect to the handle in order to operate the handle and needle set as discussed above.

Handle 41 includes forward facing, wedge-shaped, locking hooks 79 which engage slots 81 in order to lock lid 74 in a closed configuration with respect to housing 52. The wedge shape of hooks 79 allows hooks to be slightly deflected as they pass slots 81 and then snaps into slots 81 when hooks 79 are aligned with slots 81.

Accordingly, the present invention provides for an inventive handle assembly and needle set which simplifies the biopsy procedure and which is easy to use and make. The disposable handle assembly thus affords a simpler design allowing the handle to be inexpensive to make and more compact.

Although the invention has been described in detail herein, it should be understood that the invention is not limited to the embodiment herein disclosed. Various changes, substitutions and modifications may be made thereto by those skilled in the art without departing from the spirit or scope of the invention as described and defined by the appended claims.

What is claimed is:

1. A biopsy handle capable of receiving a needle set assembly having a stylet adapted for piercing and storing a tissue sample and a cannula adapted for severing and trapping the tissue sample, the biopsy handle comprising:
   a housing adapted for accepting the needle set;
   an actuator slidably attached to the housing and adapted for selectively positioning the stylet and the cannula relative to the housing; and
   said actuator includes an element which is adapted to allow the actuator to be slid in a forward and a reverse direction with respect to the housing in order to move the stylet and the cannula relative to the housing using a single digit of a single hand of a user.

2. The biopsy handle of claim 1 wherein:
   said actuator has a base that is slidably attached to said housing; and
   said element of said actuator includes a projection from said slidable base of said actuator, which projection has first and second sides, which first and second sides are adapted to be urged by the single hand of the user, with urging on the first side for moving the actuator forwardly and urging on the second side for moving the actuator rearwardly.

3. The biopsy handle of claim 1 wherein:
   said actuator includes a member that is adapted to establish the length of a sample of tissue that the stylet can take.

4. The biopsy handle of claim 1 wherein the element is a first protrusion adapted to be engaged by a user's hand.

5. The biopsy handle of claim 4 wherein said actuator includes a second protrusion that is adapted to be engaged by a user's hand.

6. A biopsy handle capable of receiving a needle set assembly having a stylet adapted for piercing and storing a tissue sample and a cannula adapted for severing and trapping the tissue sample, the biopsy handle comprising:
   a housing adapted for accepting the needle set;
   said housing having a locking lid which can be moved from an open position in order to accept the needle set into said housing to a closed and locked position in order to lockingly contain the needle set in the housing;
   said locking lid is adapted for allowing single use of the housing;
   one of said lid and said housing includes catches and the other of said lid and said housing includes receptacles which receives said catches for locking the needle set in the housing;
   said catches are wedge shaped with a ramp and a back edge; and
   wherein said ramp allows said catches to be urged into said receptacle and said back edge lock said catches in said receptacle.

7. A method of taking a tissue biopsy with a biopsy handle which includes a housing that has a movable actuator and which handle is adapted for receiving a needle set including a stylet and a cannula, the steps including:
   loading the needle set into the handle;
   using a single hand in order to hold the handle and a single digit of the single hand to move the actuator in order to lock the cannula against an urging force, and
   using the same single hand in order to continue to hold the handle and a single digit of the single hand to move the actuator in order to advance the stylet into tissue to be biopsied.

8. The method of claim 7, including the further step of:
   using the same single hand in order to continue to hold the handle and a single digit of the single hand to move the actuator to cause the cannula to be urged over the stylet in order to capture tissue.

9. The method of claim 8, including the further step of:
   using a single digit of the same single hand in order to move the actuator in order to move the cannula relative to the stylet in order to have access to any tissue captured between the stylet and the cannula.

10. A biopsy handle capable of receiving a needle set assembly having a stylet adapted for piercing and storing a tissue sample and a cannula adapted for severing and trapping the tissue sample, the biopsy handle comprising:
    a housing adapted for accepting the needle set;
    an extension attached to said housing adapted for selectively presetting a depth of travel of the stylet into the tissue sample;
    said extension having a first means adapted for urging the stylet into a tissue sample;

said extension having a second means adapted for actuating the cannula after the first means urges the stylet into a tissue sample; and said extension includes an adjustable member that is adapted for presetting the depth of travel of the stylet into the tissue sample.

11. The handle of claim 10, wherein:

said handle is adapted for one hand operation.

12. The handle of claim 10, wherein:

said extension has a portion extending therefrom which adapts the handle for one-hand operation.

13. The biopsy handle as recited in claim 10, wherein said first means comprises a stylet coupling that couples the extension to the stylet.

14. The biopsy handle as recited in claim 10, wherein said second means comprises a trip bar protrusion.

15. A biopsy handle capable of receiving a needle set assembly having a stylet adapted for piercing and storing a tissue sample and a cannula adapted for severing and trapping the tissue sample, the biopsy handle comprising:

a housing adapted for accepting the needle set;

an extension slidably attached to said housing adapted for urging the stylet and actuating the cannula;

said extension having an adjustable wheel adapted for presetting a depth of travel of the stylet into the tissue sample; and wherein said extension is adapted to be operable by a single digit of a single hand of a user.

16. A biopsy handle adapted for accepting a needle set having a stylet and a cannula, the handle comprising:

a housing;

a first guide secured to said housing;

a second guide secured to said housing;

an actuator slidably mounted on said housing;

a first pin associated with said first guide;

a second pin associated with said second guide;

said first pin adapted to engage a stylet of a needle set;

said second pin adapted to engage a cannula of a needle set;

a spring associated with said second guide and said second pin;

a pushing member that is associated with said second pin in order to urge said second pin relative to said second guide and against said spring;

said first pin and said pushing member operatively associated with said actuator such that as said actuator slides relative to said housing, said first pin and said pushing member move relative to said housing and along said first guide and said second guide, respectively in order to urge the stylet and the cannula into a first operable position;

a member that is adapted to adjust a length of travel of the stylet relative to said housing.

17. The handle of claim 16, further including:

said housing having a first locking member;

said second pin having a second locking member;

and with the stylet and the cannula in a first operable position such that said second pin is urged against said spring, said first locking member engages said second locking member in order to lock said second pin in the first operable position relative to said housing;

a trip pin;

said trip pin associated and movable with said actuator;

said trip pin being capable of contacting said first locking member in order to release said second locking member and thereby allow said spring to move said second pin and thus the cannula relative to said housing; and said member that is adapted to adjust a length of travel of the stylet relative to said housing being associated with said actuator and with said trip pin such that adjusting said member changes the position of said trip pin relative to said actuator.

18. A biopsy handle adapted for accepting a needle set having a stylet with a stylet base with a first aperture, and a cannula with a cannula base with a second aperture, with the stylet and cannula movable relative to each other as the stylet base and the cannula base move relative to each other, said biopsy handle comprising:

a housing;

a first guide rod secured to said housing and adapted to receive the stylet base adjacent thereto such that said stylet base can move along said first guide rod;

a second guide rod secured to said housing and adapted to receive the cannula base adjacent thereto such that said cannula base can move along said second guide rod;

said first guide rod and said second guide rod being substantially parallel to each other;

an actuator slidably mounted on said housing;

a first pin that is movable along said first guide rod;

a second pin that is movable along said second guide rod;

said first pin adapted to engage the first aperture of the stylet base of the needle set;

said second pin adapted to engage the second aperture of the cannula base of the needle set;

a spring associated with said second guide rod and said second pin;

a pushing member that is associated with said second pin in order to urge said second pin relative to said second guide rod and against said spring;

said first pin and said pushing member operatively associated with said actuator such that as said actuator slides relative to said housing, said first pin and said pushing member move relative to said housing and along said first guide and said second guide, respectively in order to urge the stylet and the cannula into a first operable position.

19. The handle of claim 18, further including:

said housing having a first locking member;

said second pin having a second locking member;

and with the stylet and the cannula in a first operable position such that said second pin is urged against said spring, said first locking member engages said second locking member in order to lock said second pin in the first operable position relative to said housing.

20. The handle of claim 19, further including:

a trip pin;

said trip pin associated and movable with said actuator;

said trip pin being capable of contacting said first locking member in order to release said second locking member and thereby allow said spring to move said second pin and thus the cannula relative to said housing.

21. The handle of claim 18, further including:

a member that is adapted to adjust a length of travel of the stylet relative to said housing.

22. The handle of claim 20, including:

a member that is adapted to adjust a length of travel of the stylet relative to said housing;

said member associated with said actuator and with said trip pin such that adjusting said member changes the position of said trip pin relative to said actuator.

23. A biopsy handle adapted for accepting a needle set having a stylet and a cannula, the biopsy handle comprising:

a housing;

an actuator slidably mounted to said housing;

said housing including a cavity adapted for receiving the needle set;

said actuator including a first member adapted for operably engaging the stylet;

said actuator including a second member adapted for operably engaging the cannula;

said actuator including a trip member adapted for causing the cannula to be urged over the style;

said actuator including a third member for adjusting the position of the trip member relative to the second member in order to adjust a length that the stylet extends into tissue to be sampled.

24. The biopsy handle of claim 23, further including:

said housing having a first locking member;

a second locking member which is operably associated with the second member and adapted to be operably associated with the cannula such that said second member can urge said second locking member in order to urge said cannula into a position; and said second locking member capable of lockingly engaging said first locking member in order to lock the cannula into a position and said trip member for releasing said cannula from the locked position.

25. The biopsy handle of claim 18 including:

an indicia that indicates the length that the stylet is set to extend into tissue.

26. A biopsy handle capable of receiving a needle set assembly having a stylet adapted for piercing and storing a tissue sample and a cannula adapted for severing and trapping the tissue sample, the biopsy handle comprising:

a housing adapted for accepting the needle set;

an actuator slidably attached to the housing and adapted for selectively positioning the stylet and the cannula relative to the housing; and said actuator includes an element means adapted for allowing the actuator to be slid in a forward and a reverse direction with respect to the housing in order to move the stylet and the cannula relative to the housing using a single digit of a single hand of a user.

* * * * *